(12) United States Patent
Anschütz

(10) Patent No.: US 6,200,343 B1
(45) Date of Patent: Mar. 13, 2001

(54) INTRA-OCULAR LENS WITH RESILIENTLY CONSTRUCTED HAPTIC LOOPS

(76) Inventor: Till Anschütz, Konrad-Adenauer-Strasse 3, D-76572 Gaggenau (DE)

(*) Notice: Subject to any disclaimer, the term of this patent is extended or adjusted under 35 U.S.C. 154(b) by 0 days.

(21) Appl. No.: 09/248,992

(22) Filed: Feb. 12, 1999

(30) Foreign Application Priority Data

Feb. 12, 1998 (DE) .............................. 198 05 780

(51) Int. Cl.⁷ ............................................. A61F 2/16
(52) U.S. Cl. .................... 623/6.39; 623/6.46; 623/6.54
(58) Field of Search .................. 623/6.18, 6.19, 623/6.37, 6.38–6.43, 6.46, 6.47, 6.51–6.54, 6.113

(56) References Cited

U.S. PATENT DOCUMENTS

| | | |
|---|---|---|
| 3,986,214 | 10/1976 | Krasnov . |
| 4,262,370 * | 4/1981 | Hartstein .............................. 623/6.38 |
| 4,298,996 * | 11/1981 | Barnet ................................. 623/6.43 |
| 4,615,702 | 10/1986 | Koziol et al. . |
| 4,834,751 | 5/1989 | Knight et al. . |
| 4,863,464 | 9/1989 | Dusek . |
| 5,300,117 | 4/1994 | Baikoff et al. . |
| 5,628,796 | 5/1997 | Suzuki . |

FOREIGN PATENT DOCUMENTS

| | | |
|---|---|---|
| 0061282 | 9/1988 | (EP) . |
| 0 477 109 A1 | 3/1992 | (EP) . |
| 97/27825 | 8/1997 | (WO) . |

* cited by examiner

Primary Examiner—David H. Willse
(74) Attorney, Agent, or Firm—Evenson, McKeown, Edwards & Lenahan, P.L.L.C.

(57) ABSTRACT

An intra-ocular lens having an optical lens part can be implanted in the anterior chamber of an eye in front of the iris. The lens has haptic loops which, in the implanted condition, are guided through incisions in the iris and are supported in the posterior chamber of the eye, particularly in the area of the sulcus ciliaris.

4 Claims, 1 Drawing Sheet

INTRA-OCULAR LENS WITH RESILIENTLY CONSTRUCTED HAPTIC LOOPS

BACKGROUND OF THE INVENTION

The present invention relates to an intra-ocular lens including an optical lens part which can be implanted in an anterior chamber of an eye in front of the iris. The lens includes resiliently constructed haptic loops, each of which has a radially interior loop portion connected with the optical lens part and a radially exterior loop portion which can be supported at an intra-ocular supporting point. The radially exterior loop portions are offset, in the direction of the optical axis of the optical lens part with respect to the radially interior loop portions, toward the posterior chamber of the eye. The radially exterior loop portions are guidable through incisions in an area of the outer edge of the iris and supportable on the sulcus ciliaris behind the iris. The radially interior and radially exterior loop portions are situated in two planes which are offset along the optical axis of the optical lens part, with portions of the loops which extend between the radially interior and exterior loop portions being disposed at an angle with respect to the two planes.

One intra-ocular lens is known from International Patent Document WO 97/27,825 and has haptic loops which are molded to the periphery of the lens body. Another lens, known from U.S. Pat. No. 5,628,796, has small support legs which project through openings on the periphery of the iris. A further lens, known from U.S. Pat. No. 3,986,214, also has small support legs projecting radially from the lens body.

An additional intra-ocular lens known from European Patent Document EP 061,282 B1 has an optical lens part which is implanted in the anterior chamber of the eye in front of the pupil formed by the iris. Resiliently constructed haptic loops, which are supported at three points in the chamber angle of the anterior chamber of the eye by foot plates, are used for support.

SUMMARY OF THE INVENTION

It is an object of this invention to provide an anterior chamber lens which has a simply constructed haptic system and by which a positionally stable support of the optical lens part is achieved in the eye.

According to the invention, this object is achieved by providing the haptic loops with approximately U-shapes or V-shapes with respective legs which are formed by the radially interior and exterior loop portions. The radially interior loop portions are embedded in the lens body of the optical lens part and the radially exterior loop portions are curved along concentric circular sections.

In the present invention, the haptic system is formed by threads or open loops which, with respect to the optical lens axis, have a radially interior thread portion or loop portion and a radially exterior thread portion or loop portion. The radially interior loop portion is connected with the optical lens part, and the radially exterior loop portion is used for the support in the posterior chamber of the eye, particularly on the sulcus ciliaris (ciliary groove) behind the iris. For this purpose, the radially exterior loop portions are connected with loop portions which extend diagonally with respect to the plane of the optical lens part. During implantation, the radially exterior loop portions are guided through incisions in the area of the outer edge of the iris so that they can be supported on the sulcus ciliaris behind the iris in the posterior chamber of the eye. The radially exterior loop portions are situated in a plane which extends approximately parallel to the plane in which the connection points of the interior loop portions with the optical lens part are provided.

The radially interior loop portions may be cast into the lens body of the optical lens part. However, it is also possible to mold the radially interior thread portions or loop portions to the circumference of the optical lens part. The connection points are situated at diametrical points with respect to the optical axis of the optical lens part. The connection points are preferably situated on circular sections, particularly if the open haptic loops or threads are embedded in or cast into the lens body. The lens body may consist of a foldable material, such as a silicone polymer or a hydrogel polymer. The open haptic loops or threads consist of a harder material, such as polymethylmethacrylate (PMMA). The free ends of the haptic loops may be provided with lobar thickenings for a simplified threading of the haptic loops through the incisions placed in the iris.

The invention advantageously provides an anterior chamber lens, and particularly a phakic anterior chamber lens, which is supported in the posterior chamber of the eye, preferably on the sulcus ciliaris.

BRIEF DESCRIPTION OF THE DRAWINGS

The present invention will be explained in detail by referring to an embodiment shown in the drawing figures.

DESCRIPTION OF THE PREFERRED EMBODIMENT

Figure 1:
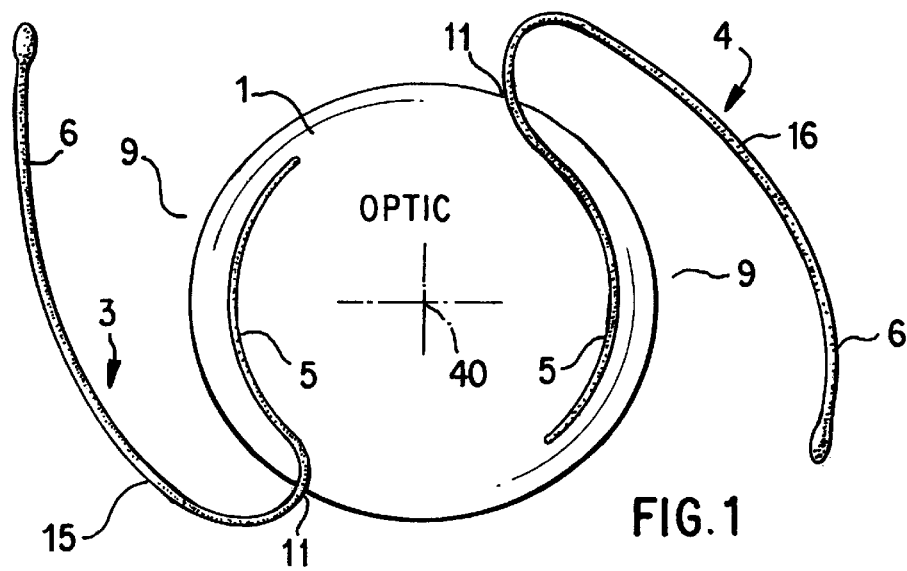
FIG. 1 is a top view of an embodiment of the invention.

The illustrated embodiment has an optical lens part 1. Open haptic loops (threads) 3 and 4 are embedded in the lens body of the optical lens part, for example, by integral casting. The threads or haptic loops are approximately U-shaped or V-shaped, with curved, approximately circular-arc-shaped loop portions in an end area on each of the respective legs. The haptic loops 3, 4 have radially exterior loop portions 6 and radially interior loop portions 5. Along a circularly curved connection point 9, the interior loop portions 5 are connected with the optical lens part 1. In the illustrated embodiment, the interior thread portions 5 are integrally cast with and embedded in the optical lens part. Casting may be accomplished, for example, during polymerization of the lens part. The connection locations or "points" 9 formed by the radially interior loop portions 5 are situated diametrically opposed to one another with respect to the optical axis 40 of the lens part 1.

Figure 2:
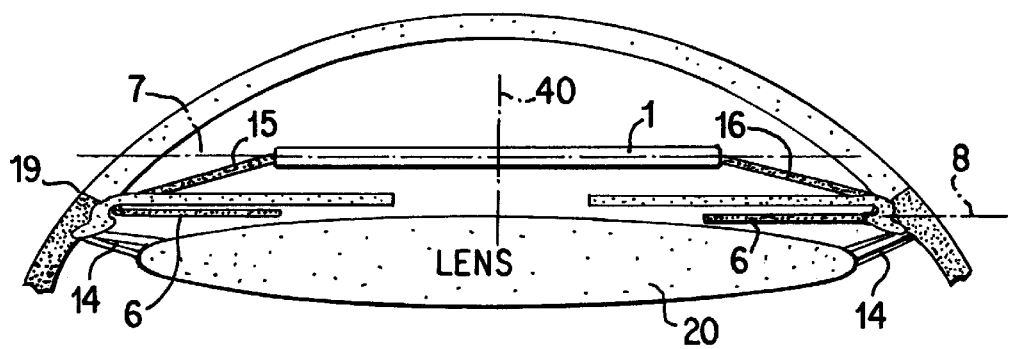
FIG. 2 is a sectional view of the embodiment in an implanted condition.

Outlet points 11 of the haptic loops from the lens body of the optical lens part are also diametrically opposed, with respect to the optical axis, on the periphery of the lens part 1. The radially interior loop portions 5 are situated in a connection plane 7 which is perpendicular with respect to the optical axis 40. The connection points 9, which are defined on the circular sections of the interior thread portions 5, are situated with the optical lens part 1 in the connection plane. The radially exterior thread portions 6 are disposed in a supporting plane 8 in which they are supported, in the sulcus ciliaris 19 behind the iris 13 and in front of the zonule fibers 14, in the eye. The two planes 7 and 8 are parallel and, in the direction of the optical axis 40, are offset with respect to one another. Loop portions 15, 16, which extend at angles with respect to the two planes 7 and 8, are situated between the radially interior thread portions 5 and the radially exterior thread portions 6. The diagonal course of the thread portions 15, 16 determines the distance of the optical lens part 1 from the iris or from the sulcus ciliaris and the natural lens 20 of the eye, as illustrated in FIG. 2.

Figure 3:
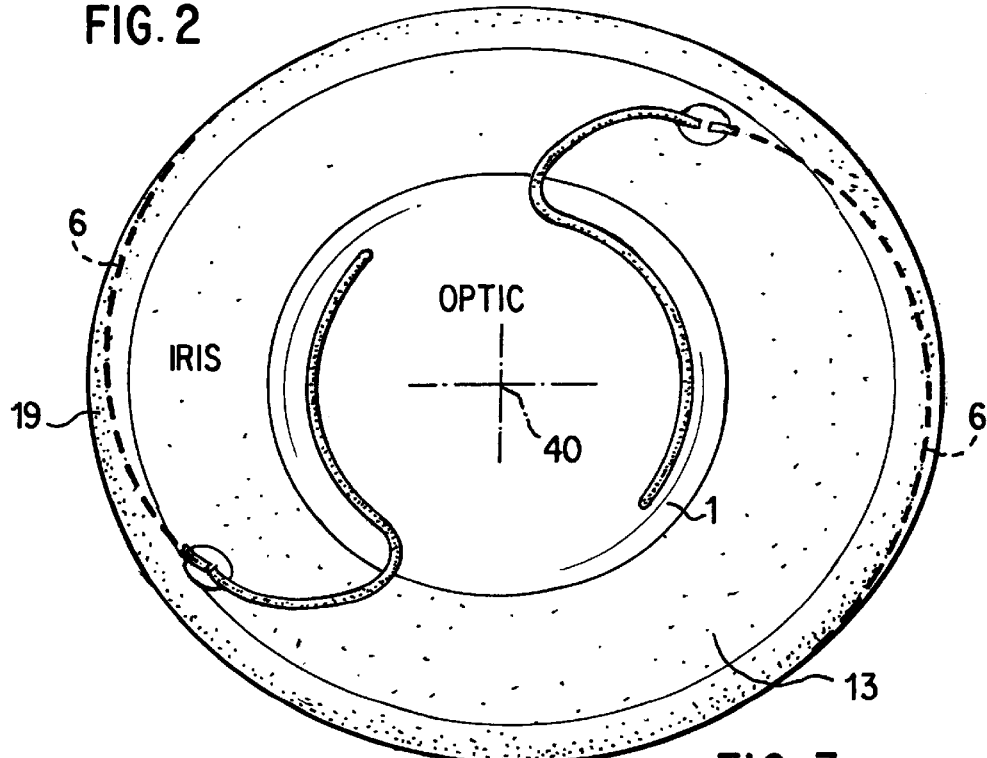
FIG. 3 is a top view of the embodiment in the implanted condition.

As shown particularly in FIG. 3, the radially exterior loop portions 6 rest within a circular section against the sulcus ciliaris. The supporting circular sections of the radially exterior loop portions 6 are preferably situated approximately concentrically with respect to the circular sections of the connection points 9. The radially interior loop portions 5 are connected with the lens part 1 at these connection points. The common center of the loop portions 5, 6 extends along the circular sections and is formed by the optical axis 40 of the lens part 1. In this manner, a balanced holding force is exercised on the optical lens part 1 by simple devices when the optical lens part 1 is supported in the anterior chamber. Consequently, the lens part 1 is arranged in the correct position in the anterior chamber, in a stable manner in front of the pupil formed by the iris 13, and in front of the natural lens 20 of the eye. This stable positioning of the optical lens part 1 is also achieved since the circular sections of the interior and exterior loop portions 5, 6 are situated diametrically with respect to one another. This is also true of corresponding points on the diagonally extending loop portions or thread portions 15, 16 which connect the interior or exterior loop portions 5, 6 with one another. The diameter of the optical lens part 1 is approximately 6.0 to 6.5 mm, and the spacing of the points of the exterior loop portions 6 which are radially the farthest to the outside is approximately 12.5 to 13.5 mm. The spacing (approximately 3 mm) of the two planes 7 and 8 in the axial direction is dimensioned such that a stable positioning of the optical lens part 1 is achieved in front of the pupil. This stable positioning is also promoted by the additional support of the haptic loops, particularly in the area of the loop portions 15, 16, on the iris.

The intra-ocular lens can be implanted as an aphakic lens after a cataract operation or as a phakic lens in front of the natural lens of the eye.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:
1. Intra-ocular lens comprising:
an optical lens part which can be implanted in an anterior chamber of an eye in front of the iris, and
resiliently constructed haptic loops, each of said loops having a radially interior loop portion connected with the optical lens part and a radially exterior loop portion which can be supported at an intra-ocular supporting point,
the radially exterior loop portions being offset, in a posterior direction of the optical axis of the optical lens part, with respect to the radially interior loop portions,
the radially interior and radially exterior loop portions being situated in two planes which are offset along the optical axis of the optical lens part, portions of the loops which extend between the radially interior and exterior loop portions disposed at an angle with respect to the two planes,
wherein the haptic loops have approximately U-shapes or V-shapes with respective legs which are formed by the radially interior and exterior loop portions each extending along circular sections,
wherein the radially interior loop portions are embedded completely along circular sections thereof in the lens part and the radially exterior loop portions are guidable through incisions in an area of the outer edge of the iris and supportable on the sulcus ciliaris behind the iris along circular sections which are concentric with the circular sections of the interior loop portions, and
wherein mutually corresponding loop portions of the haptic loops are situated diametrically relative to one another with respect to the optical axis.
2. Intra-ocular lens according to claim 1, wherein thickenings are provided at the free ends of the exterior loop portions.
3. Intra-ocular lens comprising:
an optical lens part which can be implanted in an anterior chamber of an eye in front of the iris, and
resiliently constructed haptic loops, each of said loops having a radially interior loop portion connected with the optical lens part and a radially exterior loop portion which can be supported at an intra-ocular supporting point,
the radially exterior loop portions being offset, in a posterior direction of the optical axis of the optical lens part, with respect to the radially interior loop portions,
the radially interior and radially exterior loop portions being situated in two planes which are offset along the optical axis of the optical lens part, portions of the loops which extend between the radially interior and exterior loop portions disposed at an angle with respect to the two planes,
wherein the haptic loops have approximately U-shapes or V-shapes with respective legs which are formed by the radially interior and exterior loop portions each extending along circular sections,
wherein the radially interior loop portions are molded completely along circular sections thereof to the circumference of the optical lens part and the radially exterior loop portions are guidable through incisions in an area of the outer edge of the iris and supportable on the sulcus ciliaris behind the iris along circular sections which are concentric with the circular sections of the interior loop portions, and
wherein mutually corresponding loop portions of the haptic loops are situated diametrically relative to one another with respect to the optical axis.
4. Intra-ocular lens according to claim 3, wherein thickenings are provided at the free ends of the exterior loop portions.

* * * * *